United States Patent [19]

Kiernan et al.

[11] 4,432,995

[45] * Feb. 21, 1984

[54] 5-[2-ETHYLAMINO)-1-HYDROXYLETHYL] ANTHRANILONITRILE AND THE USE THEREOF IN MEAT PRODUCING ANIMALS

[75] Inventors: Jane A. Kiernan, Kendall Park; Pamela K. Baker, Hopewell, both of N.J.

[73] Assignee: American Cyanamid Company, Stamford, Conn.

[ * ] Notice: The portion of the term of this patent subsequent to Oct. 4, 2000 has been disclaimed.

[21] Appl. No.: 365,138

[22] Filed: Apr. 5, 1982

Related U.S. Application Data

[63] Continuation-in-part of Ser. No. 219,055, Dec. 22, 1980, Pat. No. 4,407,819, which is a continuation of Ser. No. 181,255, Aug. 25, 1980, abandoned, which is a continuation-in-part of Ser. No. 143,070, Apr. 24, 1980, abandoned, which is a continuation-in-part of Ser. No. 66,909, Aug. 16, 1979, abandoned, which is a continuation-in-part of Ser. No. 219,054, Dec. 22, 1980, Pat. No. 4,404,222, which is a continuation-in-part of Ser. No. 143,069, Apr. 24, 1980, abandoned, which is a continuation-in-part of Ser. No. 66,908, Aug. 16, 1979, abandoned.

[51] Int. Cl.³ .................. A61K 31/275; C07C 121/50; C07C 121/60; C07C 121/74

[52] U.S. Cl. ................. 424/304; 260/465 E
[58] Field of Search ............ 424/248.56, 248.57, 424/267, 274, 330, 304; 260/465 E

[56] References Cited

U.S. PATENT DOCUMENTS

| | | | |
|---|---|---|---|
| 3,536,712 | 10/1970 | Keck et al. | 424/248.56 |
| 3,574,211 | 4/1971 | Keck et al. | 424/330 |
| 3,818,011 | 6/1974 | Baile et al. | 424/330 |
| 3,925,475 | 12/1975 | Horrom | 424/330 |
| 3,950,393 | 4/1976 | Keck et al. | 424/330 |
| 4,119,710 | 10/1978 | Engelhardt et al. | 424/330 |
| 4,214,001 | 7/1980 | Engelhardt et al. | 424/322 |
| 4,228,187 | 10/1980 | Lambelin et al. | 424/330 |
| 4,276,304 | 6/1981 | Ikezaki et al. | 424/330 |

FOREIGN PATENT DOCUMENTS

2351281 4/1975 Fed. Rep. of Germany .

OTHER PUBLICATIONS

Chem. Abst. 71, 89890(b)(1969)—Slanger et al.
Chem. Abst. 73, 33,781(r)(1970)—Autumes–Rodrigues.

Primary Examiner—Douglas W. Robinson
Attorney, Agent, or Firm—H. G. Jackson

[57] ABSTRACT

The invention is the compound 5-[2-(ethylamino)-1-hydroxyethyl] anthranilonitrile and its use for increasing lean meat deposition; improving the lean meat to fat ratio, increasing growth rate and improving the efficiency of feed utilization in meat producing animals.

6 Claims, No Drawings

5-[2-(ETHYLAMINO)-1-HYDROXYLETHYL] ANTHRANILONITRILE AND THE USE THEREOF IN MEAT PRODUCING ANIMALS

This application is a continuation-in-part of co-pending Ser. No. 219,055 filed Dec. 22, 1980, now U.S. Pat. No. 4,407,819 which is a continuation-in-part of Ser. No. 181,255 filed Aug. 25, 1980 (now abandoned) which is a continuation-in-part of Ser. No. 143,070 filed Apr. 24, 1980 (now abandoned) which is a continuation-in-part of Ser. No. 66,909 filed Aug. 16, 1979 (now abandoned). Further the application is a continuation-in-part of co-pending Ser. No. 219,054 filed Dec. 22, 1980, now U.S. Pat. No. 4,404,222 which is a continuation-in-part of Ser. No. 181,254 filed Aug. 25, 1980 (now abandoned) which is a continuation-in-part of Ser. No. 143,069 filed Apr. 24, 1980 (now abandoned) which is a continuation-in-part of Ser. No. 66,908 filed Aug. 16, 1979 (now abandoned).

SUMMARY OF THE INVENTION

Substitution products of certain 1-(aminodihalophenyl)-2-amino ethanes and the acid addition salts thereof are disclosed in U.S. Pat. No. 3,536,712, issued on Oct. 27, 1970. Specifically, patentees disclose methods for the synthesis of said compounds and state that said compounds are useful for enhancing the blood circulation, and as bronchodilators, analgesics, sedatives, antipyretics, antiphlogistics and antitussives in warm-blooded animals.

Other related 1-(aminodihalophenyl)-2 aminoethanols and their derivatives are disclosed in Japanese Kokai No. 77 83,619 (Chemical Abstracts, 87, 201061r), German Offenlegungsschrift No. 2,804,625 (1979), German Offenlegungsschrift No. 2,157,040 (1973), German Offenlegungsschrift No. 2,261,914 (1974), European Patent Application No. 8,715 (1980), Netherlands Patent Application No. 7,303,612 (1973). These application disclose uses selected from analgesics, broncholytic, antiinflammatory, uterine spasmolytic, β-mimetic and/or β-blocking activities, antispasmolytic activity on cross-striped muscle structure, for tocology, reducing blood pressure by peripheral vasodilation and mobilizing body fat, and for treating allergies.

The invention is the compound 5-[2-(ethylamino)-1-hydroxyethyl] anthranilonitrile of the formula

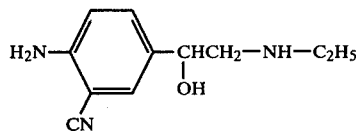

and optically active isomers, and non-toxic pharmacologically acceptable acid addition salts thereof; its use for increasing lean meat deposition, improving the lean meat to fat ratio, increasing growth rate and improving the feed efficiency of feed utilization in meat producing animals; and animal feed composition containing the compound.

EXAMPLE 1

5-[2-Ethylamino)-1-hydroxyethyl] anthranilonitrile

A 23.9 gram-sample of 4-amino-3-cyanophenacyl bromide is added to a solution containing 100 mL of ethylamine in 150 mL of ethanol at a temperature that is below 0° C., and the mixture is allowed to gradually rise to 12°–13° C. The solution is stirred for a total of 0.5 hour and then cooled further in an ice bath before 10 g of $NaBH_4$ is added. The mixture is then stirred overnight at ambiant temperature. Water (50 mL) is then added; and, after 0.75 hour, the mixture is evaporated in vacuo to remove the ethanol and extracted twice with 800 mL of $CH_2Cl_2$. The $CH_2Cl_2$ extracts are combined, dried over $Na_2SO_4$, and evaporated to dryness in vacuo to afford a yellowish solid. This solid is triturated with a mixture of 50 mL of ether and 50 mL of hexane and filtered to afford 10.06 g of solid, mp 121°–6° C. This solid is dissolved in 300 mL of acetone, decolorized with activated carbon, filtered through diatomaceous earth. The filter cake is further washed with 300 mL of acetone. The filtrate is evaporated to dryness in vacuo to a volume of about 20 mL, and 10 mL of hexane is added. The solid is then collected by filtration to afford 5.55 g of the title compound, mp 126°–130° C.

EXAMPLE 2

Evaluation of test compounds as antilipogenic agents and animal growth promoters—Mouse tests CFI female mice from Carworth Farms are received when they are six weeks old. They are housed ten to a cage in air-conditioned rooms (22° C. to 25° C.) with automatically controlled lights, 14 hours on and 10 hours odd. The basal diet used in these studies is Purina Laboratory Chow (see description below), which is supplied ad libitum.

The following is a description of the diet to which the growth-promoting compounds were added.

DIET

Guaranteed Analysis

Crude protein not less than: 23.0%
Crude fat not less than: 4.5%
Crude fiber not more than: 6.0%
Ash not more than: 9.0%

Ingredients

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewer's dried yeast, thiamin, niacin, vitamin A supplement, calcium carbonate, dicalcium phosphate, iodized salt, ferric ammonium citrate, iron oxide, manganous oxide, cobalt carbonate, copper oxide, zinc oxide. Water is also allowed ad libitum.

Thriteen days after arrival, the mice are weighed in groups of ten and assigned at random to the different treatments. The concentration of the different compounds in the diet is indicated in the following tables. Twelve days later the mice are weighed again and the experiment terminated. At least three cages (30 mice) of untreated controls are included in each test. Test data are provided in Table I below wherein data are reported as percent body fat, percent change in body fat from controls and gain per mouse in grams.

Percent Body Fat Determination of Mice

A. Preparation of Carcasses:

Stomach and intestines are removed from each mouse. All other viscera, including skin and fur, remain intact. Each cage of mice (10) are weighed and added to a 1000 ml beaker and autoclaved at 120° C. (1.05 kg cm$^{-2}$ pressure) for 30 minutes. Carcasses from each cage are then blended and homogenized. The homogenate is weighed and duplicate 5-gram samples are removed for analysis.

B. Fat Analysis:

Fifteen milliliters (ml) of concentrated hydrochloric acid is added to each 5-gram samples and mixed well. Samples are heated in an 84° C. water bath for 2 hours. To extract the fat, thirty ml of petroleum ether is added to each sample, 15 ml at a time, and mixed well on a Vortex mixer. The aqueous and organic phases are separated by low speed centrifugation and the ether layer (containing fat) is extracted into tared 30 ml beakers. After evaporating to dryness the beaker containing fat is reweighed to determine grams of fat per five grams of homogenate. Total body fat in the carcass is calculated as follows:

$$\% \text{ Fat} = \frac{\left[\begin{array}{c}\text{grams fat}\\\text{in sample}\end{array}\right] \left[\begin{array}{c}\text{grams total}\\\text{homogenate}\end{array}\right]}{\left[\begin{array}{c}\text{gram weight}\\\text{of sample}\end{array}\right] \left[\begin{array}{c}\text{carcass weight}\\\text{of mice (g)}\end{array}\right]} \times 100$$

Antilipogenic Evaluation of test compounds—Mouse Study

CFI female mice, 55 days old, are weighed in groups of 10 and allotted to cages to minimize weight variation among cages. Treatments are randomly assigned to cages.

Each of the treatments are tested in 3 replicates, i.e., in 3 cages of 10 mice each. There are 10 cages of 10 control mice each. Drugs are mixed in the diet at the dosage level indicated. Feed and water are offered ad libitum for 12-day test period. Feed spilled is collected during the test period. At the end of the test period, the collected feed is weighed and the mean feed consumption per cage of ten mice is determined for each treatment. The mice are weighed as a group of 10 and the weight gain determined. The mice are sacrificed by cervical dislocation. The right uterine fat pad of each mouse is removed. The fat pads for each cage of 10 mice are weighed as a unit.

To establish the correlation between the percent reduction in fat pad weights of treated animals and percent reduction in total body fat of treated animals, animals from several treatment groups are evaluated for total body fat using the body fat determination described in Example 2. Data obtained are reported in Table I for those groups upon which such determination had been made. From percent reduction in fat pad weight and the total fat determinations for the groups tested, it can be seen that a reduction in fat pad weights of animals is generally indicative of a reduction of total body fat of the treated animals.

TABLE I

Antilipogenic Agent and Growth Enhancement Evaluation in Mice

| Compound | ppm | grams gain | control | Fat Pad Wt. % ± control |
|---|---|---|---|---|
| $NH_2$—⟨⟩—CHCH$_2$—NH—C$_2$H$_5$ \| \| CN OH | 200 | 12.0 | −0.83 | −56.42 |
| | 100 | 17.9 | 47.93 | −43.00 |
| | 50 | 22.6 | 86.78 | −32.54 |
| | 20 | 24.1 | 99.17 | 5.04 |
| | 12 | 21.1 | 74.38 | 3.97 |
| | 6 | 23.1 | 90.41 | −10.65 |
| | 3 | 19.2 | 58.68 | −17.09 |

We claim:

1. 5-[2-(ethylamino)-1-hydroxyethyl] anthranilonitrile of the formula $$H_2N-\underset{CN}{\underset{|}{\bigcirc}}-\underset{OH}{\underset{|}{CHCH_2}}-NH-C_2H_5,$$

optically active isomers, or non-toxic, pharmacologically acceptable acid addition salts thereof.

2. A method for increasing lean meat deposition, improving the lean meat to fat ratio, increasing the growth rate and improving the efficiency of feed utilization in warm-blooded animals which comprises orally or parenterally administering to the animals an effective amount of the compound 5-[2-(ethylamino)-1-hydroxyethyl] anthranilonitrile, optically active isomers or non-toxic pharmacologically acceptable acid addition salts thereof.

3. A method according to claim 2 wherein the compound is orally administered to the animal in an animal feed containing 0.01 to 400 grams of compound per ton of feed.

4. A method according to claim 2 wherein the compound is parenterally administered as a subcutaneous implant containing a sufficient amount to provide the animal with from 0.001 to 100 mg/kg/day of body weight of the compound.

5. An animal feed composition comprising an edible animal feed containing from 0.01 grams to 400 grams of the compound 5-[2-(ethylamino)-1-hydroxyethyl] anthranilonitrile, optically active isomers or non-toxic, pharmacologically acceptable acid addition salts thereof.

6. An animal feed supplement comprising about 10% to 25% by weight of the compound 5-[2-(ethylamino)-1-hydroxyethyl] anthranilonitrile or an optically active isomer, or non-toxic, pharmacologically acceptable acid addition salts thereof.

* * * * *